United States Patent
Furumoto et al.

(10) Patent No.: US 6,187,145 B1
(45) Date of Patent: Feb. 13, 2001

(54) METHOD FOR PROCESS MANAGEMENT IN PAPER AND CARDBOARD MANUFACTURE

(75) Inventors: Herbert Furumoto, Erlangen; Ulrich Gerdemann, Langensendelbach; Gerhard Zeiner, Stuttgart, all of (DE)

(73) Assignee: Siemens Aktiengesellschaft, Munich (DE)

( * ) Notice: Under 35 U.S.C. 154(b), the term of this patent shall be extended for 0 days.

(21) Appl. No.: 08/913,736

(22) PCT Filed: Mar. 19, 1996

(86) PCT No.: PCT/DE96/00476

§ 371 Date: Dec. 31, 1997

§ 102(e) Date: Dec. 31, 1997

(87) PCT Pub. No.: WO96/29468

PCT Pub. Date: Sep. 26, 1996

(30) Foreign Application Priority Data

Mar. 23, 1995 (DE) ............................................. 195 10 009

(51) Int. Cl.[7] ................................. D21F 11/00; D21F 7/00
(52) U.S. Cl. ................................. 162/198; 162/252
(58) Field of Search ..................................... 162/198, 252

(56) References Cited

U.S. PATENT DOCUMENTS

| 4,098,641 |   | 7/1978 | Casey et al. . |
|---|---|---|---|
| 5,082,529 | * | 1/1992 | Burk ..................................... 162/198 |
| 5,220,172 |   | 6/1993 | Berthold et al. . |
| 5,282,131 |   | 1/1994 | Rudd et al. . |
| 5,486,996 | * | 1/1996 | Samad et al. ........................ 364/152 |
| 5,841,671 | * | 11/1998 | Furumoto ....................... 364/471.01 |

FOREIGN PATENT DOCUMENTS

| 0 137 696 | 4/1985 | (EP) . |
|---|---|---|
| 95/08019 | 3/1995 | (WO) . |

* cited by examiner

Primary Examiner—Christopher A. Fiorilla
(74) Attorney, Agent, or Firm—Kenyon & Kenyon

(57) ABSTRACT

A method and apparatus for using a neural network to control a paper or paper board production machine. By using spectrum measuring devices, the characteristics of the starting materials for the paper and board production and/or their intermediate or final products are registered and the values fed to a neural network. The network provides statements concerning the paper and board quality, from which signals for the feedback and/or feedforward control of the production process may be derived.

26 Claims, 6 Drawing Sheets

METHOD FOR PROCESS MANAGEMENT IN PAPER AND CARDBOARD MANUFACTURE

This application in the U.S. national stage application of International Application No. PCT/OE96/00476 having an international filing date of Mar. 19, 1996.

FIELD OF THE INVENTION

The invention relates to a method and a device for the process management of a paper machine for the production of paper and/or board, using at least one measuring device for registering physical characteristic values and at least one regulating or controlling device for the operating means used in the paper machine.

BACKGROUND OF THE INVENTION

In the earlier international Patent Application WO 95/08019 A1, which is not a prior publication, a device is proposed for operating an installation specifically for the production of deinked pulp. The installation includes at least one waste paper preparation means, downstream of which a paper machine or at least one dewatering machine is connected. In this case, measuring devices for registering spectral and/or physical characteristic values of the waste paper suspension are already used. Furthermore, regulating or controlling devices are used there for the operating means of the waste paper preparation means. There is also at least one state analyser, designed in the form of one or more parallel neural networks, for the waste paper suspension. The analyzer, by means of the characteristic values of the measuring device, supplies controlled variables for process management to the regulating or controlling devices of the operating means for the waste paper preparation means.

In the case of the device described above for the production of deinked pulp, using as great a proportion as possible of waste paper, there is in particular the problem that the quality of waste paper introduced into the installation fluctuates severely. For example, there can be, in the respective mixture of waste paper, sharply variable proportions of, for example, coloured illustrated paper, gray newsprint, white paper, contaminated paper, old books, for example with adhesive residues, such as telephone directories, cartons, packages, coated papers and contaminations of all types. The device previously described in the earlier Patent Application solves these problems in a satisfactory manner for the waste paper preparation means.

EP-A-0,137,696 discloses a method and an associated device for registering the water content of a paper web during production, in which, via an optical infrared measurement, use is made of the fact that water has an absorption band at 1.94 $\mu$m. To this end, a measuring channel and a reference channel having a different wavelength than the water absorption band is used. In addition, U.S. Pat. No. 5,282,131 discloses a system for regulating a pulp washing plant, in which a neuron network is employed to verify predictable process parameters. In the case of both of these documents, therefore, only some aspects of paper production are addressed.

OBJECTS AND SUMMARY OF THE INVENTION

An object of the present invention is to use the measurement principle on which the above described device is based directly in a paper machine. The object is achieved, according to the invention, in that, using the measuring device, spectral characteristic values are registered at different wavelengths on the operating materials of the paper machine. The operating materials are the starting material directly before the flow box on the paper machine and/or the intermediate or final product. The signals from the measuring device for the spectral characteristic values are evaluated by at least one neural network and statements about the product quality are derived therefrom. The statements are, in particular, the quality parameters of the paper or of the board. Signal variables are derived from the statements about the product quality. The signal variables may be used, on the one hand, for feedback control in the so-called stock preparation upstream of the paper machine, and on the other hand, for the feed forward control of the paper machine itself.

In the case of feedback control, the parameters of the stock preparation are adjusted to produce the stock quality necessary for an intended paper or board quality. In the case of feedforward control, on the other hand, the operating means of the paper machine are controlled so that an intended paper or board quality is achieved with a given stock quality.

The result of the invention is to provide, for the first time, the possibility of an on-line measurement using the spectrometer in a paper machine. By suitable evaluation, with determination of the quality values of the paper or the board, the quality-influencing parameters in the stock preparation for the paper machine can also be influenced. The delay times which were produced with the previously normal laboratory measurement are thus dispensed with.

In the associated arrangement, spectroscopes or spectrometers are used, in particular for picking up spectral distributions or overall spectra. The neural networks are used within the context of the invention, specifically for the evaluation of spectral characteristic values. Either the diffuse backscatter intensity or the diffuse transmitted intensity of selected spectral ranges is used as input variables for the neural networks. Further parameters of the stock suspension or of the paper or board, for example, consistency, moisture, grammage and the like, may also advantageously be used as input variables for the neural networks. Output variables from the neural networks are mechanical quality parameters of the paper or board produced, such as in particular, the so-called CMT value, the breaking length, the burst pressure, and other factors which are significant for the practical suitability of the paper. The neural networks can be trained using quality parameters measured off-line in the laboratory.

BRIEF DESCRIPTION OF THE DRAWINGS

The foregoing and other objects and advantages of the present invention will be better understood with reference to the following detailed description of several embodiments thereof, which is illustrated by way of example, in the accompanying drawings, wherein.

DETAILED DESCRIPTION OF THE INVENTION

In the figures, identical or identically acting parts have corresponding reference symbols.

Figure 1:
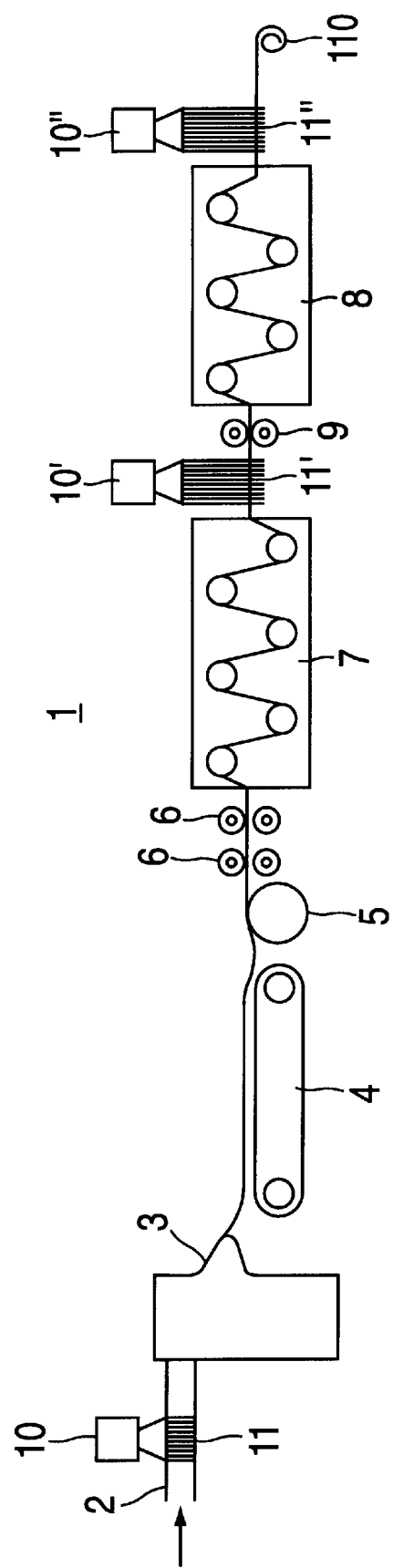
FIG. 1 schematically illustrates an embodiment of the invention in the context of a paper producing machine.

In FIG. 1 an installation for producing paper is designated by 1, which essentially comprises the so-called stock entry 2, the actual paper machine with flow box 3, a downstream wire mesh conveyor belt 4 for the transport of the wet paper webs, further roller tracks such as 5 and 6 for drying and winding up a paper web 110 and a size press 9. In particular, the size press 9 can be arranged between drying devices 7 and 8. Installations of this type for producing paper are known and in use in practice in a wide range of technical configurations.

In the installation according to FIG. 1 there is a first spectrometer 10 in the region of the stock inlet 2. The measuring area 11 of the spectrometer 10 is directed onto the stock suspension that is used for the starting material for the paper production. A second spectrometer 10' has its measuring area 11' directed onto the paper web 110 upstream of the size press 9. Furthermore, a third spectrometer 10" is arranged with its measuring area 11" downstream of the size press 9, the measuring are 11" may be directed onto the sized paper before the adjacent wind-up device, which is not shown in detail.

Figure 2B:
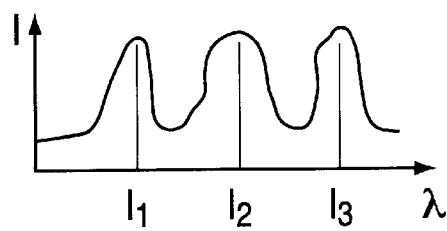
FIG. 2b illustrates the use of certain preferred wavelengths as inputs to the neural networks.
Figure 2A:
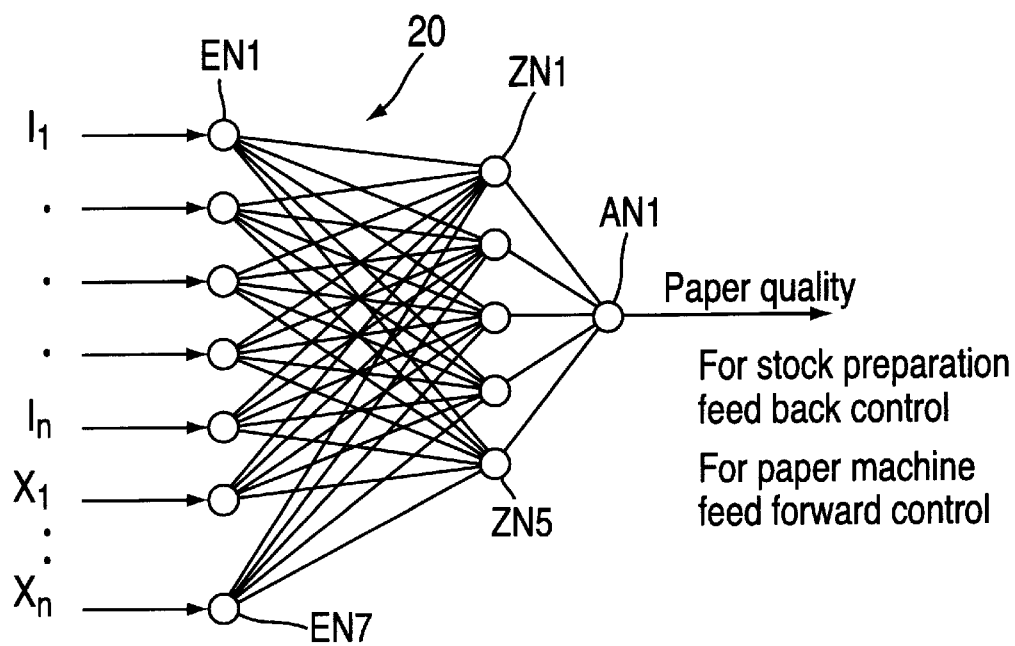
FIGS. 2a and 3 schematically illustrate two partial neural networks for use in FIG. 1

In FIG. 2a a three-layer neural network in designated by 20, and, for example, comprises input neurons EN1 to EN7 and further neurons ZN1 to ZN5 and an associated output neuron AN1. Using the neural network 20, the spectrum from the first spectrometer 10 is evaluated. The backscatter intensities $I_1$ to $I_n$ from preferred wavelengths $\lambda_i$ of the schematic diagram in FIG. 2b are used as inputs for the neural network 20. Statements about the quality of the paper to be produced may be obtained from the wavelength intensities $I_i$ with i=1, . . . , n. The statements of the paper quality of output AN1 can be used, on the one hand, for the feedback control in the stock preparation and, on the other hand, for feedforward control in the paper machine 1 itself.

Figure 3:
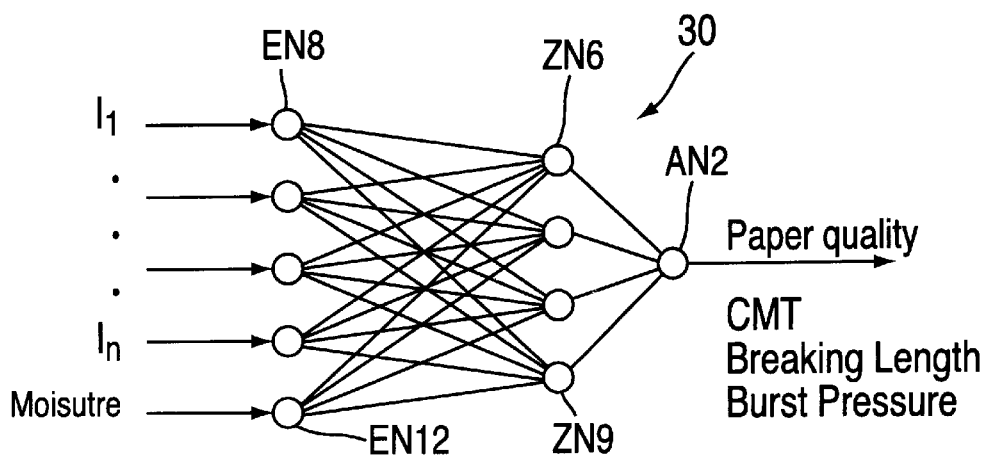

Shown in FIG. 3 is another three-layer neural network 30, which has input neurons EN8 to EN12 and further neurons ZN6 to ZN9 and an output neuron AN2. Using this second neural network 30, data from the spectrometers 10' and 10" are evaluated in a similar manner to that in FIG. 2a. It is also advisable to use the moisture 31 of the paper web 110 as a measured variable as a further input variable. Hence, statements about the product quality of the finished paper or board may be obtained on output AN2. Furthermore, mechanical parameters, such as the so-called CMT factor, the breaking length, and the burst pressure, can also be obtained.

It is also possible to provide, for the two further spectrometers 10' and 10", one dedicated partial neural network each. The neural networks according to FIGS. 2 and 3 can also be combined, the reliability of the derivation of the measured variables being improved by their interlinking.

Alternative possibilities for use of spectrometers in the context of paper and board production are set forth in FIGS. 4 to 7. For each of FIGS. 4 to 7 there is a unit 50 for stock preparation, a so-called central stock area 70, a paper machine 100, which corresponds to the paper machine 1 according to FIG. 1, and a neural network 200, which is assigned to the paper machine 100 and corresponds to the neural network 20 of FIG. 2a. The units 50, 70, 100 and 200 are integrated into a functional loop.

Figure 4:
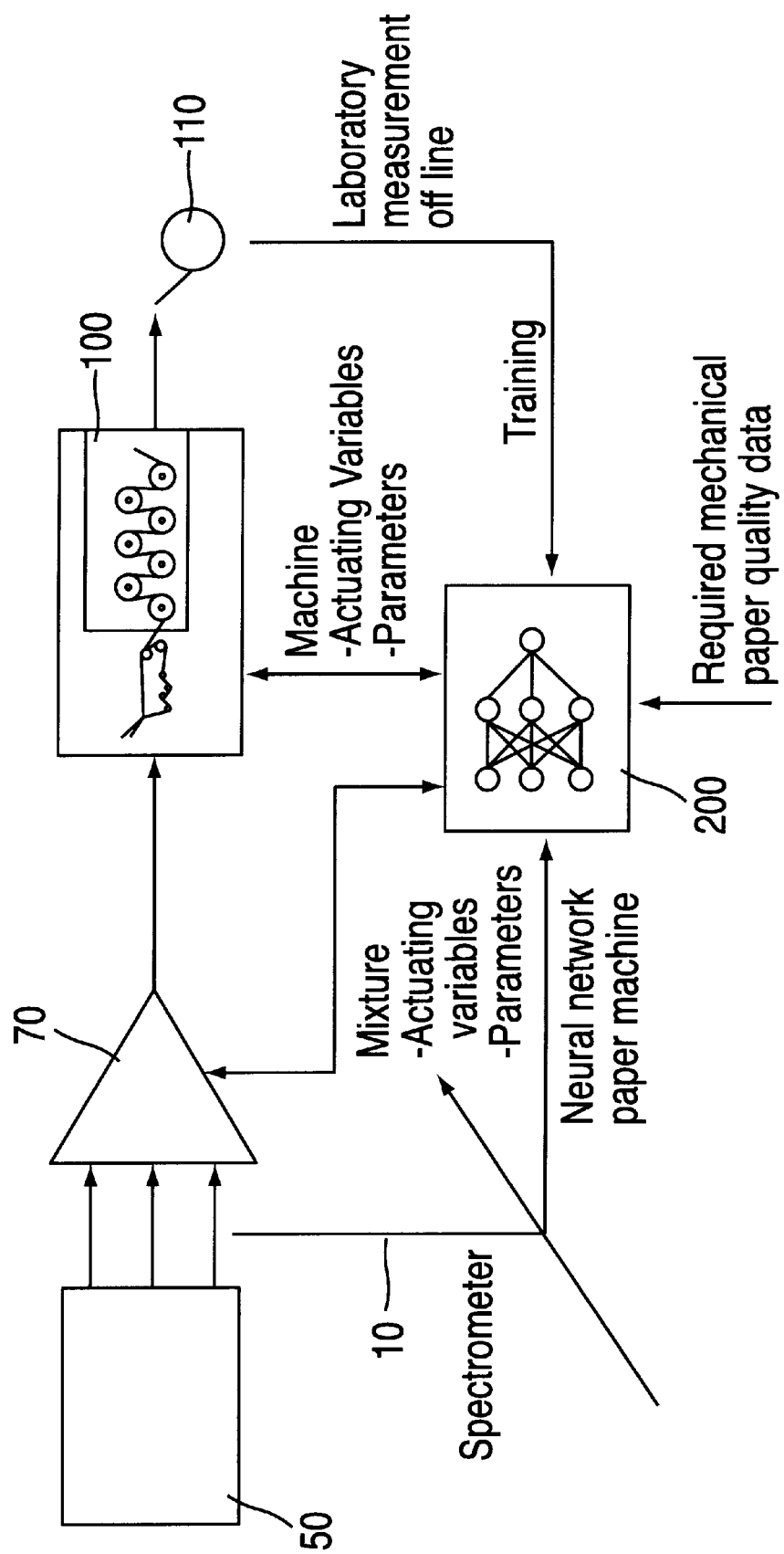
FIGS. 4 to 7 show alternative embodiments for utilizing the data provided by spectrometers.

In FIG. 4 the spectrometer 10 according to FIG. 1 is assigned to the unit 50 for stock preparation. There, it is possible, for example, to register pulp or different waste paper materials, which is indicated by means of the parallel arrows. Via the central stock area 70, suitable output material passes to the paper machine 100. In addition to the signals from the spectrometer, the machine parameters and actuating variables and the data about the required paper quality are fed to the neural network 200. Following off-line training via laboratory measurements on finished paper, the required mixing parameters and actuating variables for the output stock are given to the central stock area 70 using the neural network 200.

Figure 5:
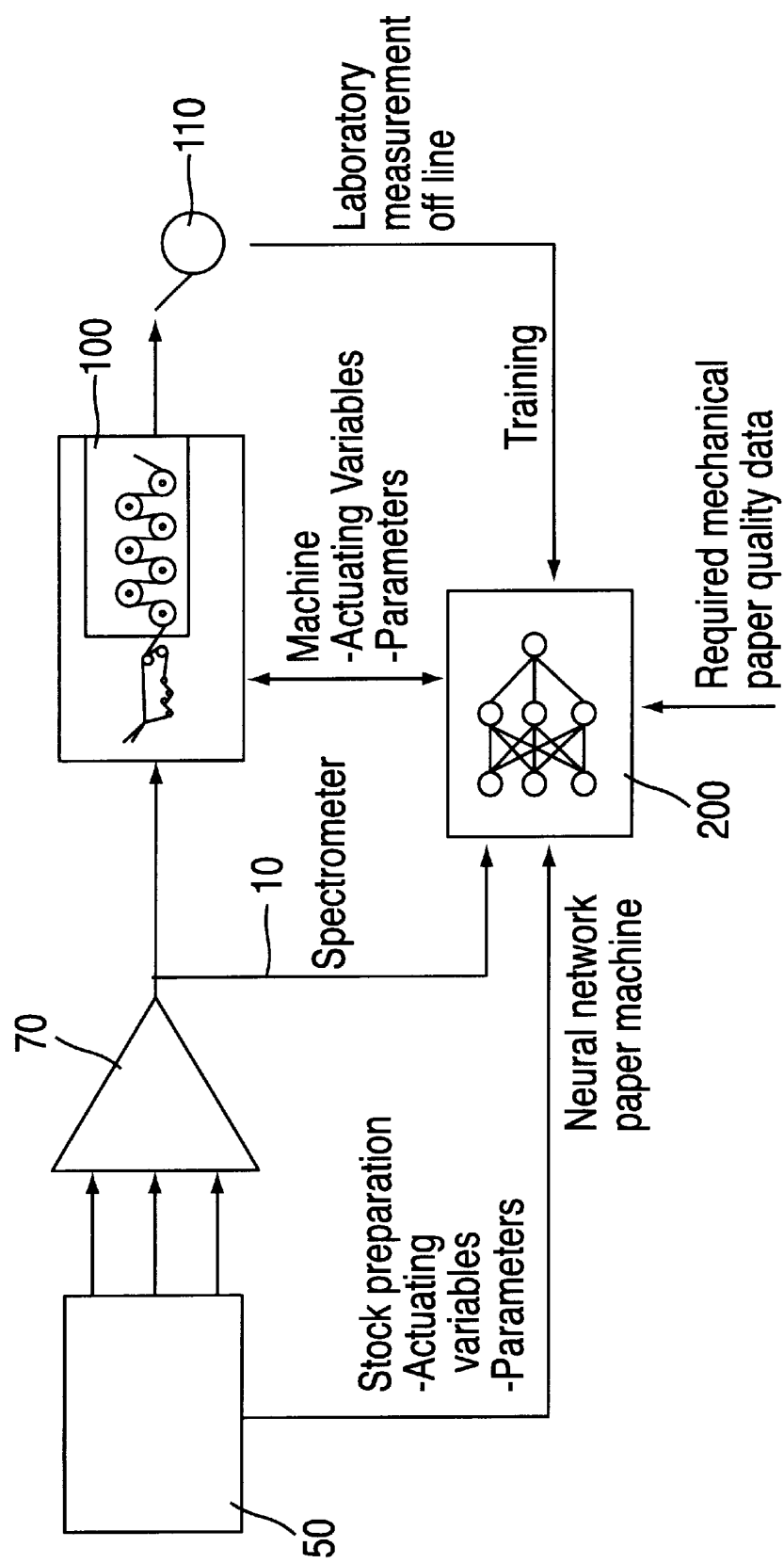

In FIG. 5, the measurement using the spectrometer 10 takes place at the stock inlet for the paper machine 100, that is to say downstream of the central stock area 70. With a construction of the neural network 200 which is in principle identical, the result here is the possibility of generating actuating signals, such as actuating variables and parameters for the stock preparation 50, on the one hand, and actuating variables for the paper machine 100, on the other hand.

Figure 6:
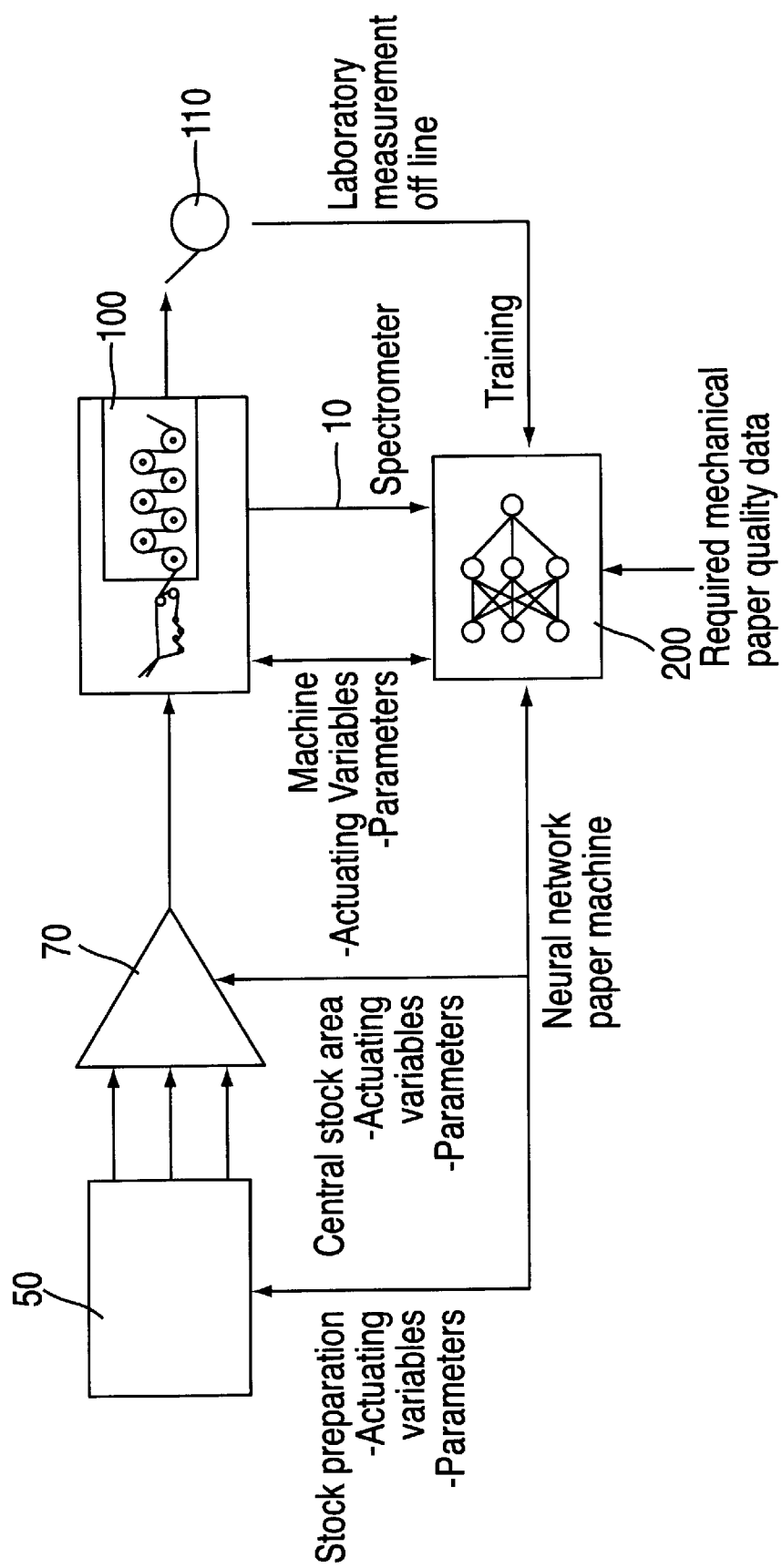

In the case of the arrangement according to FIG. 6, the spectrometer 10 is used on the finished paper or board emergent within the paper machine 100. In accordance with FIG. 6, using the neural network, it is likewise possible to obtain actuating variables for the paper machine 100, as well as actuating signals for the stock preparation 50 or the central stock area 70.

Figure 7:
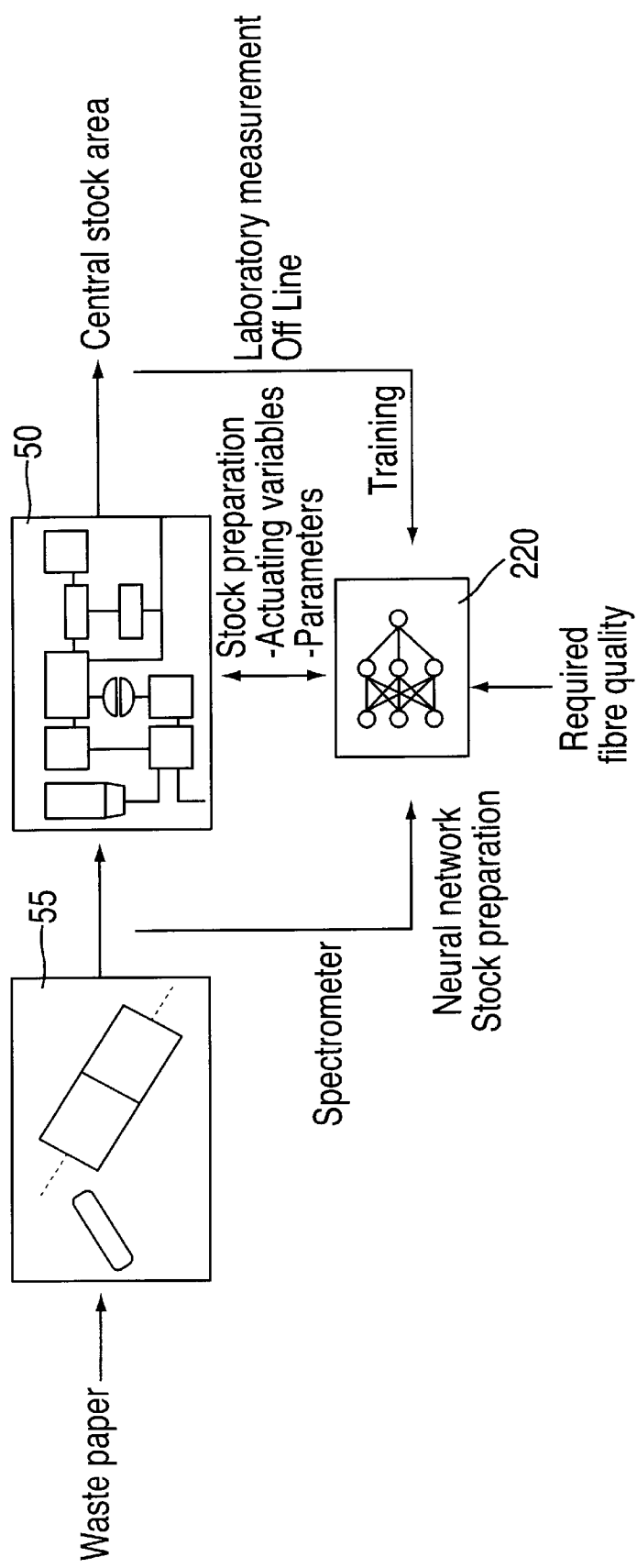

In the case of the alternatives shown in FIGS. 4 to 6, the neural network 200 is in each case directly assigned to the paper machine 100, the required mechanical paper quality data being predetermined as important characteristic variables. In FIG. 7, an example is specified which specifically relates to the stock preparation 50, that is to say the unit 50 of FIGS. 4 to 6. In addition to the unit 50 for the stock preparation, having known individual elements, such as a so-called pulper, a refiner or the like, there is here, moreover, a stock pulping unit 55. The stock pulping unit 55 essentially prepares waste paper and mixes it in specific proportions with a suitable pulp suspension.

In FIG. 7 the unit 50 for the stock preparation is assigned a neural network 220, to which the required fibre qualities are input as characteristic variables. Using the spectrometer 10, in this case measurements are made on the pulped stock before the actual stock preparation 50, and the measured intensity signals are entered into the neural network 220. Following suitable training of the neural network 220, suitable actuating signals for the stock preparation 50 may be obtained using the measured values.

In the individual examples, it was shown that as a result of on-line measurement using one or more spectrometers and evaluation using one or more neural networks, as well as determination of the quality values of the paper or board to be produced, the quality determining parameters of the stock preparation and of the paper machine can be influenced on-line. In contrast to previous approaches utilizing discontinuous methods using laboratory measurements, the present invention avoids delay times.

What is claimed is:

1. A method for the process management of a paper machine for the production of a paper product, the paper machine having a flow box and at least one measuring device for registering characteristic values, and a regulating or controlling device for controlling the paper machine, the method comprising the steps of:

registering spectral characteristic values at different wavelengths of operating materials of the paper machine using at least one measuring device, the operating materials being at least one of a starting material directly before the flow box of the paper machine, intermediate products of the paper machine or final products of the paper machine;

evaluating signals from the at least one measuring device with at least one neural network;

deriving statements about a mechanical quality parameter of the paper product from the evaluated signals; and deriving control signals from the statements about the mechanical quality parameter of the paper product for feedback control in a stock preparation and/or for feed forward control in the paper machine.

2. The method according to claim 1, wherein the spectral characteristic values are diffuse backscatter intensities of selected spectral regions.

3. The method according to claim 1, wherein the spectral characteristic values are diffuse transmitted intensities of selected spectral regions.

4. The method according to claim 1, wherein the spectral characteristic values of stock suspensions fed to the paper machine are registered.

5. The method according to claim 4, wherein the spectral characteristic of the stock suspension are registered continuously.

6. The method according to claim 1, wherein the spectral characteristics values of paper or board running on the paper machine are registered.

7. The method according to claim 6, wherein the spectral characteristics of the paper or the board are registered continuously.

8. The method according to claim 11, further comprising the step of:

training the at least one neural network using the quality parameters of the paper or of the board, as measured in a laboratory.

9. The method according to claim 1, having a central stock area for stock preparation for the paper and board production, further comprising the step of:

carrying out stock mixing in the central stock area in accordance with the spectral characteristic values of individual streams or with reference to the overall spectrum of the stocks leaving the central stock area.

10. A process for converting a xylem-based material into a finished paper product, comprising the steps of:

optically scanning the xylem-based material with a spectrometer;

passing signals representative of the spectrum information obtained by the spectrometer to a neural network;

analyzing the signals in the neural network to derive information concerning a mechanical quality parameter of the xylem-based material; and using the derived information to generate signals for controlling the process.

11. The process of claim 10, wherein the optically scanned material is taken from a flow box of a paper machine.

12. The process of claim 10, wherein the optical scan is of an intermediate product of the process.

13. The process of claim 10, wherein the optical scan is of a final product of the process.

14. The process of claim 10, wherein optical scans are taken of both the final product of the process and an intermediate product of the process.

15. The process of claim 10, wherein optical scans are taken of both an intermediate product of the process and a starting material.

16. The method of claim 10, wherein the intensities of specific wavelengths of light obtained during the scan are registered and passed to the neural network for the generation of statements regarding characteristics of the xylem-based material.

17. A process for converting a xylem-based material into a paper product, comprising the steps of:

optically scanning the xylem-based material with a first spectrometer;

passing optical data obtained by the spectrometer representative of a mechanical quality parameter of the xylem-based material to a neural network;

analyzing the signals in the neural network to derive information concerning the xylem-based material; and using the derived information to generate signals for controlling the process.

18. The process of claim 17 wherein the generated signals are used to control stock preparation.

19. The process of claim 17 wherein the mechanical quality parameters are registered.

20. The process of claim 17 wherein the mechanical quality parameter includes a breaking length.

21. The process of claim 17 wherein the mechanical quality parameter includes a burst pressure.

22. The process of claim 17 wherein the mechanical quality parameter includes a CMT value.

23. The process of claim 17 further comprising:

optically scanning the xylem-based material with a second spectrometer.

24. A method for the process management of a paper machine for the production of a paper product, the paper machine having a flow box, at least one measuring device for registering characteristic values, and a regulating or controlling device for controlling the paper machine, the method comprising the steps of:

registering spectral characteristic values at different wavelengths of stock suspensions fed to the paper machine using at least one measuring device;

evaluating signals from the at least one measuring device with at least one neural network;

deriving statements about the quality of the paper product from the evaluated signals; and, deriving control signals from the statements about the quality of the paper product for feedback control in a stock preparation and/or for feed forward control in the paper machine.

25. The method according to claim 24, wherein the spectral characteristics of the stock suspension are registered continuously.

26. The method according to claim 24, wherein the spectral characteristics are taken from a flow box.

* * * * *